(12) United States Patent
Kobayashi

(10) Patent No.: US 9,855,138 B2
(45) Date of Patent: Jan. 2, 2018

(54) INTRAOCULAR LENS INSERTION DEVICE

(71) Applicant: KOWA COMPANY, LTD., Aichi (JP)

(72) Inventor: Kenichi Kobayashi, Aichi (JP)

(73) Assignee: Kowa Company, Ltd., Nagoya-shi, Aichi (JP)

( * ) Notice: Subject to any disclaimer, the term of this patent is extended or adjusted under 35 U.S.C. 154(b) by 152 days.

(21) Appl. No.: 14/648,119

(22) PCT Filed: Nov. 29, 2013

(86) PCT No.: PCT/JP2013/082183
§ 371 (c)(1),
(2) Date: May 28, 2015

(87) PCT Pub. No.: WO2014/084355
PCT Pub. Date: Jun. 5, 2014

(65) Prior Publication Data
US 2015/0313709 A1    Nov. 5, 2015

(30) Foreign Application Priority Data

Nov. 29, 2012   (JP) .................................. 2012-260423

(51) Int. Cl.
*A61F 2/16*   (2006.01)
*A61F 9/00*   (2006.01)

(52) U.S. Cl.
CPC ............ *A61F 2/167* (2013.01); *A61F 2/1678* (2013.01)

(58) Field of Classification Search
CPC .......... A61F 2/16; A61F 2/167; A61F 2/1678; A61F 9/00
See application file for complete search history.

(56) References Cited

U.S. PATENT DOCUMENTS 5,616,148 A * 4/1997 Eagles .................... A61F 2/167
606/107
6,010,510 A  1/2000 Brown et al.
(Continued)

FOREIGN PATENT DOCUMENTS

EP    1832247 A1    9/2007
EP    2161005 A1    3/2010
(Continued)

OTHER PUBLICATIONS

First Office Action, including Search Report dated May 4, 2016, issued in corresponding Chinese Patent Application No. 201380062526.6, dated May 12, 2016.
(Continued)

*Primary Examiner* — Victor Nguyen
(74) *Attorney, Agent, or Firm* — Knobbe, Martens, Olson & Bear, LLP

(57) ABSTRACT

The intraocular lens insertion tool includes a nozzle main body having a nozzle portion 15, a stage portion capable of disposing the intraocular lens 2 in the nozzle main body, and a plunger 60 that presses the intraocular lens 2 set in the stage portion by a leading end, thereby releasing the intraocular lens 2 into an eyeball. The leading end portion 10a of the nozzle portion 15 is obliquely cut so that, as it goes to the front side from the optical axis rear side of intraocular lens 2, the position of the end surface is located on the front side, and at the leading end 61d of the plunger 60, a protruding portion 61e is provided which protrudes to the front side so as to be able to place the surface of the optical axis rear side of the intraocular lens 2.

6 Claims, 12 Drawing Sheets

(56) References Cited

U.S. PATENT DOCUMENTS

| | | |
|---|---|---|
| 2007/0173860 A1 | 7/2007 | Iwasaki |
| 2007/0270881 A1 | 11/2007 | Hishinuma et al. |
| 2007/0270945 A1* | 11/2007 | Kobayashi ............ A61F 2/1664 623/6.12 |
| 2012/0221102 A1 | 8/2012 | Tanaka et al. |
| 2013/0338676 A1 | 12/2013 | Marunaka et al. |

FOREIGN PATENT DOCUMENTS

| | | |
|---|---|---|
| EP | 2343029 A1 | 7/2011 |
| JP | 8-24282 A | 1/1996 |
| JP | 2007-307082 A | 11/2007 |
| JP | 2008-012016 A | 1/2008 |
| JP | 2009-28223 A | 2/2009 |
| JP | 2009-066249 A | 4/2009 |
| JP | 2009-090026 A | 4/2009 |
| JP | 2009-153915 A | 7/2009 |
| JP | 2012-050713 A | 3/2012 |
| WO | WO 2007/087104 A1 | 8/2007 |
| WO | WO 2011/048631 A1 | 4/2011 |
| WO | WO 2012/081421 A1 | 6/2012 |
| WO | WO 2012/086797 A1 | 6/2012 |

OTHER PUBLICATIONS

Extended European Search Report issued in corresponding European Patent Application No. 13858851.2, dated May 18, 2016.
International Search Report for International Application No. PCT/JP2013/082183, dated Jan. 7, 2014.
Decision on Rejection issued in corresponding Chinese Patent Application No. 201380062526.6, dated Nov. 30, 2016.
Notification of Reasons for Refusal for corresponding Japanese Patent Application No. 2014-549920, dated Sep. 5, 2017.

* cited by examiner

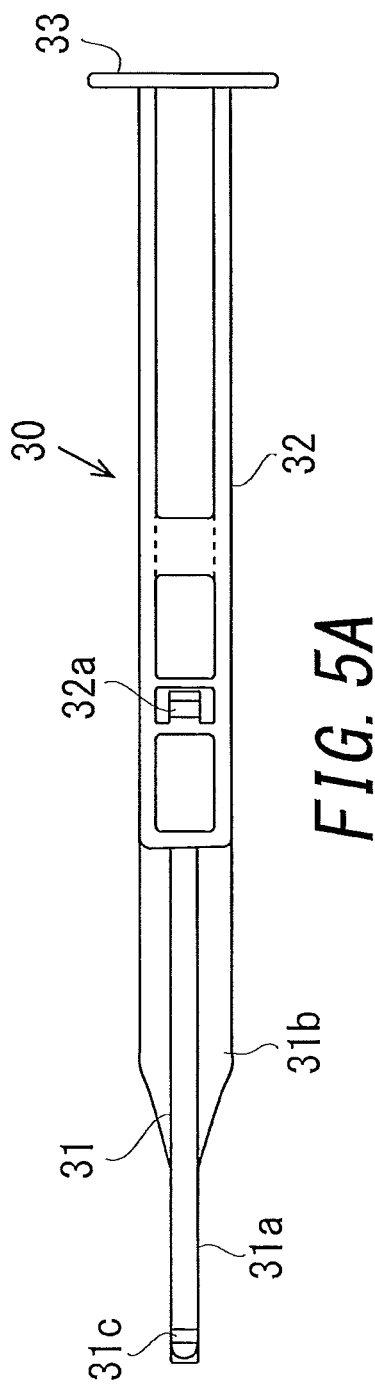
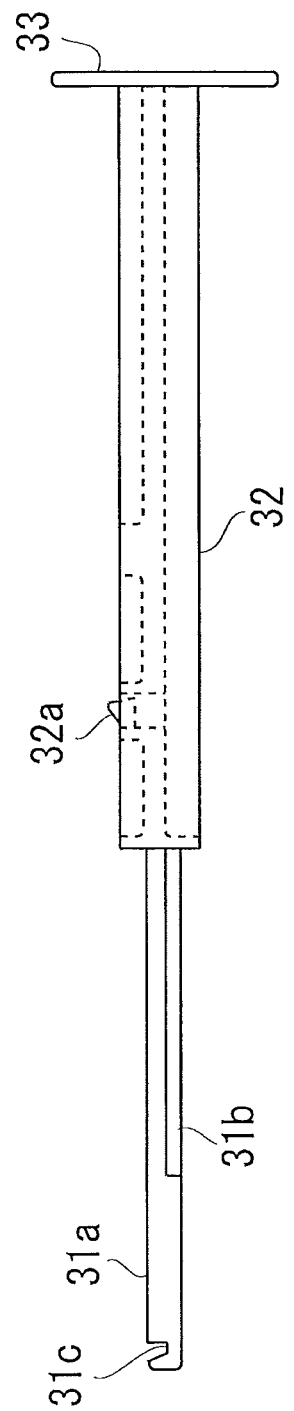
FIG. 5A
FIG. 5B

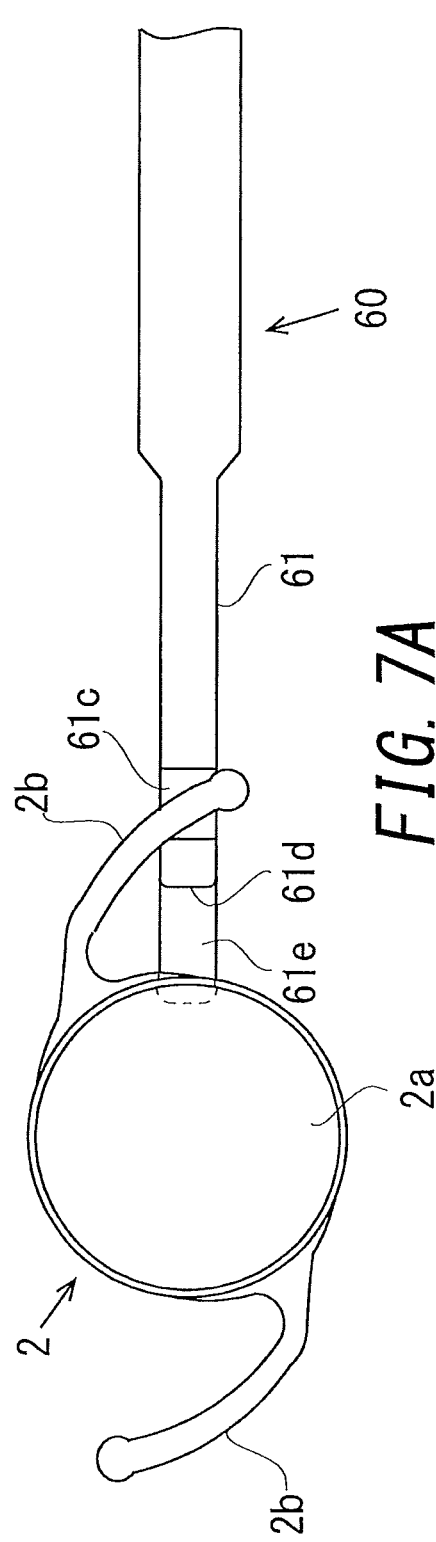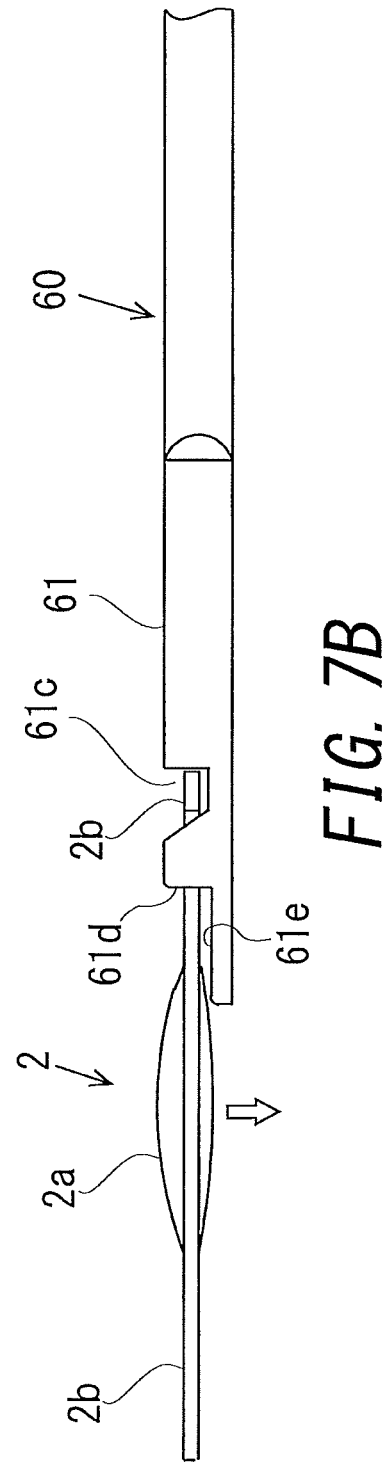
FIG. 7A
FIG. 7B

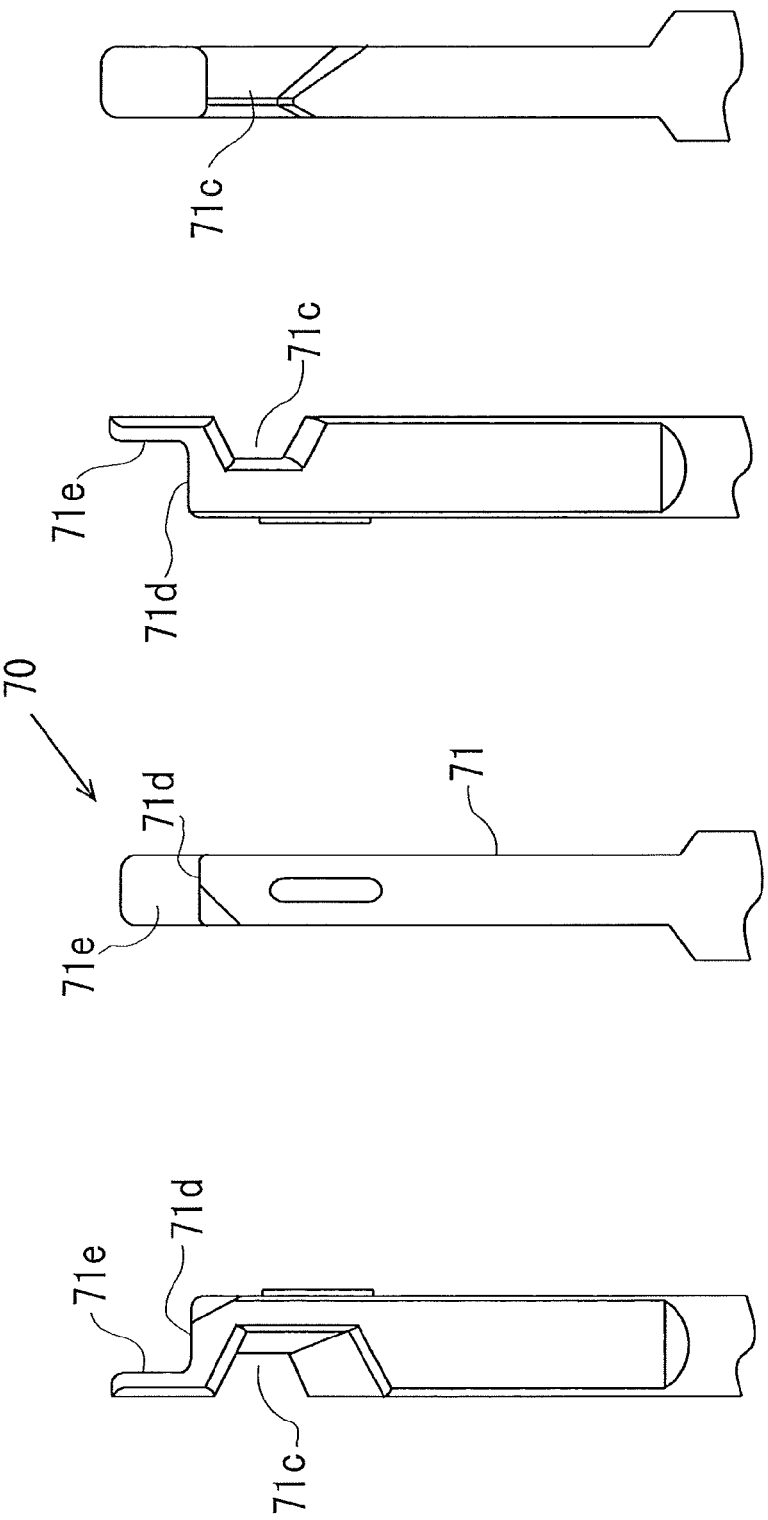

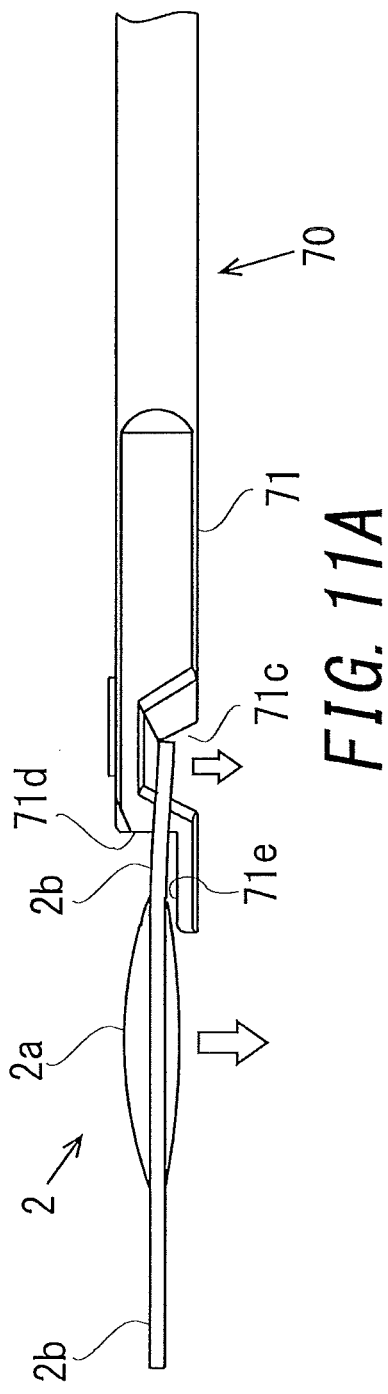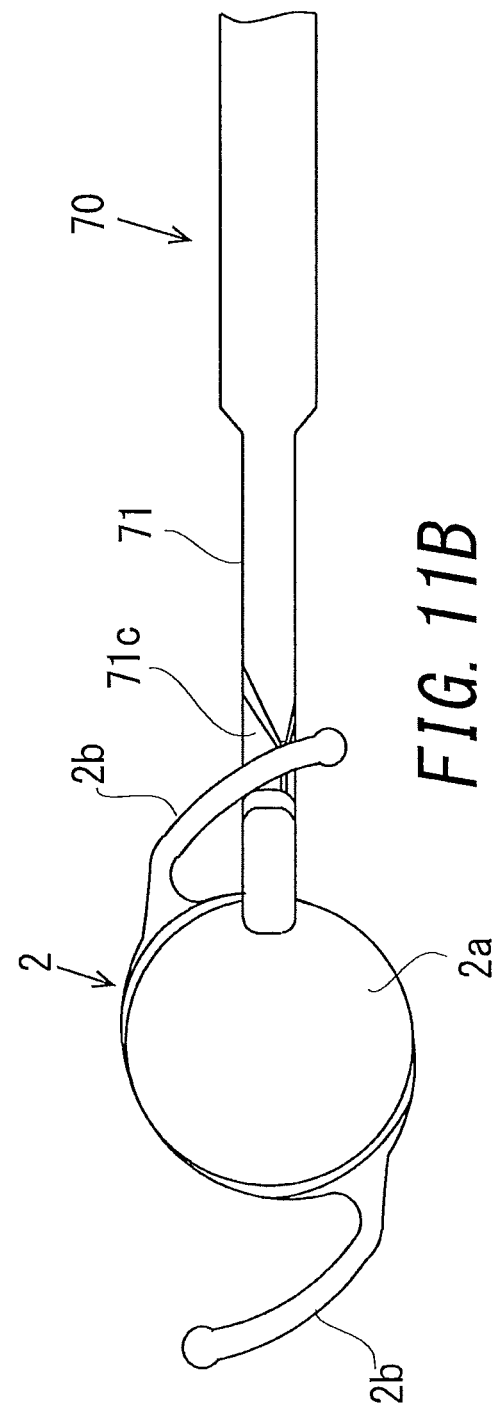
FIG. 11A
FIG. 11B

INTRAOCULAR LENS INSERTION DEVICE

TECHNICAL FIELD

The present invention relates to an intraocular lens insertion device for inserting an intraocular lens into an eyeball of a patient.

BACKGROUND ART

Conventionally, in a surgery such as a cataract surgery, a treatment has been performed in which an incision is provided in an ocular tissue such as a cornea (sclera) and an anterior capsule portion in the eyeball, an intracapsular crystalline lens is extracted and removed via the incision, and thereafter, an intraocular lens substituting the crystalline lens is inserted into the eye and disposed in the capsule from the incision.

Especially, in recent years, when inserting the intraocular lens into the eyeball from the incision, in many cases, an insertion device as illustrated below has been used. That is, a leading end opening of an insertion tube provided at a leading end portion of a device main body is inserted into the eyeball through the incision, and the intraocular lens is extruded from the leading end opening of the insertion tube by a rod-shaped plunger in the state of being slightly deformed in the device main body, thereby inserting the intraocular lens into the eyeball. By using such an insertion device, since it is possible to simply insert the intraocular lens into the eyeball by the use of the incision formed for extraction and removal of the crystalline lens, it is possible to simplify the surgery, and it is possible to suppress an occurrence of astigmatism and an occurrence of infectious disease after surgery.

Incidentally, in the insertion operation of the intraocular lens, when releasing the intraocular lens into the eyeball from the leading end opening of the insertion tube of the insertion device, in some cases, it has been difficult to stabilize the posture of the intraocular lens. That is, in some cases, since the intraocular lens may rotate (for example, forward roll) when being released from the leading end opening of the insertion tube and cannot be released while keeping a desired posture within the eyeball, the burden of posture adjustment of the intraocular lens within the eyeball after releasing the intraocular lens has increased.

Also, when releasing the intraocular lens from the leading end opening of the insertion tube, in some cases, the lens has been interposed between an inner wall of the insertion tube and a plunger, and the smooth release of the intraocular lens has been disturbed.

CITATION LIST

Patent Literature

Patent Literature 1: JP 08-024282 A
Patent Literature 2: JP 2009-028223 A

SUMMARY OF INVENTION

Technical Problem

The present invention has been made in view of the above-described conventional problems, and an object thereof is to provide a technique capable of more smoothly releasing the intraocular lens from the leading end of the insertion device, while maintaining the posture of the intraocular lens, when inserting the intraocular lens into the eyeball.

Solution to Problem

According to the present invention, there is provided an intraocular lens insertion device that includes: a device main body that has an insertion tube to be inserted into an incision formed in an ocular tissue and is formed in a substantially cylindrical shape; a housing portion that is provided integrally or separately in the device main body and is able to dispose the intraocular lens in the device main body by housing the intraocular lens; and a plunger that is pushed to the device main body and presses the intraocular lens housed in the housing portion by a leading end, thereby releasing the intraocular lens from the leading end of the insertion tube into an eyeball, the intraocular lens being inserted into the eyeball by releasing the intraocular lens from the leading end of the insertion tube inserted into the eyeball from the incision into the eyeball, wherein the leading end of the insertion tube is obliquely cut so that its partial region is located on a front side in an insertion direction of the intraocular lens, and at the leading end of the plunger, in a portion on an opposite side to the region of the leading end of the insertion tube when viewed from the front side in the insertion direction of the intraocular lens when inserting the intraocular lens, a protruding portion is provided which protrudes to the front side in the insertion direction of the intraocular lens so as to be able to place a part of the intraocular lens.

According to this configuration, by pushing the plunger into the device main body, when pressing the intraocular lens by the leading end of the plunger and releasing the intraocular lens from the leading end of the insertion tube, in the state of holding the intraocular lens by the region on the more front side in the insertion direction of the insertion tube and the protruding portion of the plunger, the intraocular lens can be released from the leading end of the insertion tube, and it is possible to suppress the unstable posture of the intraocular lens when releasing. Also, since it is possible to make the lens main body of the intraocular lens hard to be detached from the leading end of the plunger when releasing, when releasing the intraocular lens from the insertion tube, it is possible to suppress a situation in which the intraocular lens is detached from the leading end of the plunger and is interposed between the device main body and the plunger. As a result, when releasing the intraocular lens from the leading end of the insertion tube, it is possible to stabilize the posture of the intraocular lens, and it is possible to more smoothly release the intraocular lens into the eyeball.

Further, in the present invention, the leading end of the insertion tube may be obliquely cut so that, as the leading end goes toward the front side from an optical axis rear side of the intraocular lens housed in the housing portion, a position of an end surface is located on a more front side in the insertion direction of the intraocular lens, and the protruding portion may be provided so as to be able to place a surface of the optical axis rear side of the intraocular lens when inserting the intraocular lens.

According to this configuration, when pressing the intraocular lens by the leading end of the plunger and releasing the intraocular lens from the leading end of the insertion tube by pushing the plunger into the device main body, the optical axis direction front side of the intraocular lens can be supported by the leading end portion of the insertion tube, and meanwhile, the optical axis direction rear side of the intraocular lens can be supported by the protruding portion of the plunger. As a result, in the state of being held from the front and rear in the optical axis direction, the intraocular lens can be released from the leading end of the insertion tube, and it is possible to suppress the rotation (for example, forward rolling or rearward rolling) of the intraocular lens when releasing.

Also, when releasing, since the lens main body of the intraocular lens is supported by the protruding portion of the plunger from the optical axis direction rear side, and a direction perpendicular to the optical axis is similarly pressed by a portion other than the protruding portion of the leading end of the plunger, the lens main body of the intraocular lens can be made to be hardly detached from the leading end of the plunger. As a result, when releasing the intraocular lens from the insertion tube, it is possible to more reliably suppress a situation in which the intraocular lens is detached from the leading end of the plunger and is interposed between the device main body and the plunger.

As a result, when releasing the intraocular lens from the leading end of the insertion tube, it is possible to more stabilize the posture of the intraocular lens, and it is possible to more smoothly release the intraocular lens into the eyeball.

Further, the present invention may further include a lens deforming unit for deforming the intraocular lens so as to be convexed to the optical axis rear side, when the intraocular lens is released into the eyeball from the leading end of the insertion tube by pressing the intraocular lens housed in the housing portion by the plunger.

Here, when pressing the intraocular lens by the leading end of the plunger and moving it from the housing portion to the leading end of the insertion tube, the cross section of the device main body becomes generally smaller as it goes to the leading end side. Moreover, the intraocular lens is deformed so as to surround the axis in the movement direction so as to be convexed to the optical axis front side or be convexed to the optical axis rear side in accordance with a change in the cross-sectional shape. In the present invention, in such a case, a lens deforming unit is included which promotes the deformation so that the intraocular lens is convexed to the optical axis rear side, that is, the protruding portion side.

Thus, when the intraocular lens is released from the leading end of the insertion tube, it is possible to more reliably place the convexed portion of the intraocular lens on the protruding portion. As a result, it is possible to more stabilize the posture of the intraocular lens when released from the leading end of the insertion tube.

Further, in the present invention, the intraocular lens insertion device may be a preset type insertion device in which the intraocular lens is housed in the housing portion in advance in a manufacturing process, and which is distributed in a state in which the intraocular lens is housed. According to this configuration, it is possible to more rapidly and more smoothly or stably insert the intraocular lens into the eyeball of the patient.

In addition, the above-described means for solving the problems of the present invention can be used in combination as much as possible.

Advantageous Effects of Invention

According to the present invention, when inserting the intraocular lens into the eyeball, it is possible to more smoothly release the intraocular lens from the leading end of the insertion device, while maintaining the posture of the intraocular lens.

BRIEF DESCRIPTION OF DRAWINGS

FIGS. 5A and 5B are diagrams illustrating a schematic configuration of a conventional plunger.

FIGS. 7A and 7B are diagrams illustrating a positional relation between the plunger and the intraocular lens in the first example of the present invention.

FIGS. 10A to 10E are diagrams illustrating the vicinity of the leading end of the plunger in a second example of the present invention.

FIGS. 11A and 11B are diagrams illustrating a positional relation between the plunger and the intraocular lens in the second example of the present invention.

DESCRIPTION OF EMBODIMENTS

Embodiments of the present invention will be described below with reference to the drawings.

First Example

Figure 1A:
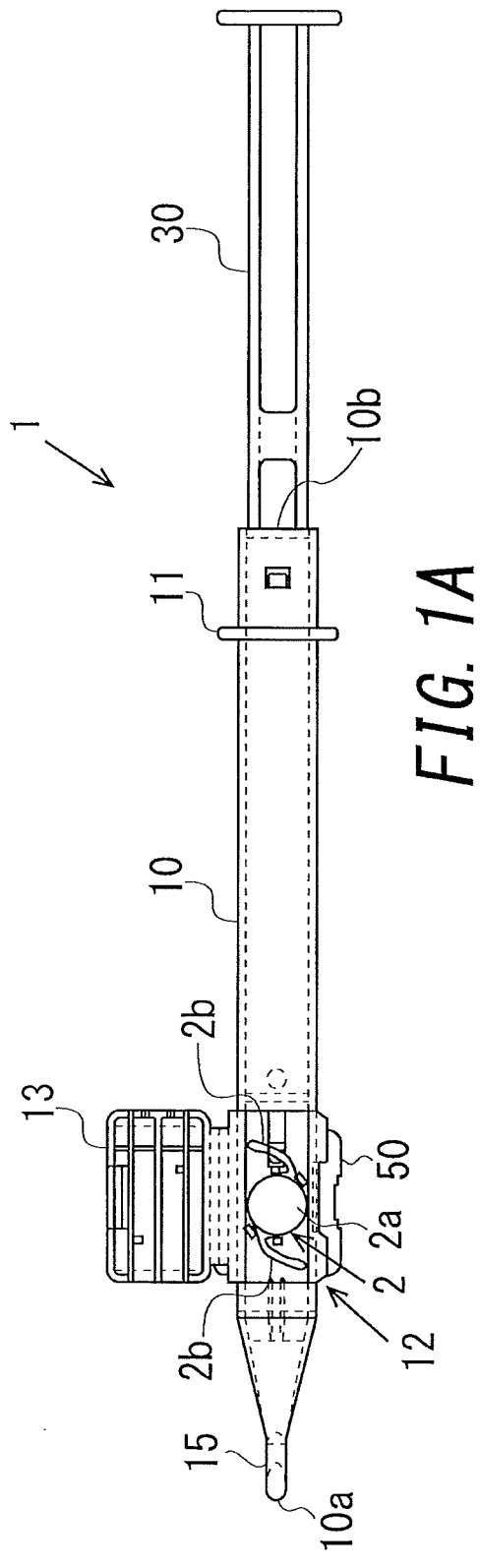
FIGS. 1A and 1B are diagrams illustrating a schematic configuration of a conventional intraocular lens insertion device.
Figure 1B:
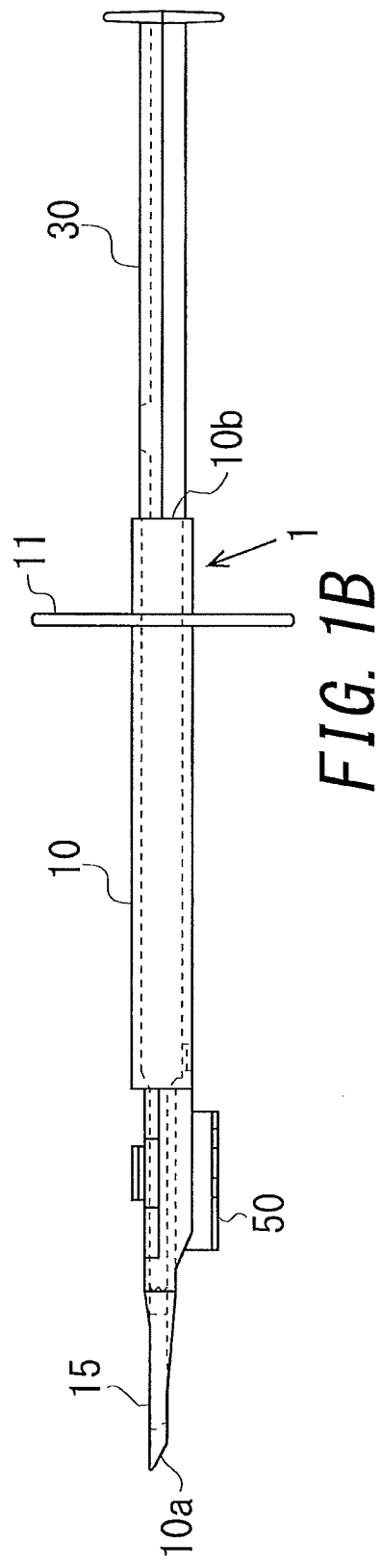

FIGS. 1A and 1B illustrate a schematic configuration of a conventional intraocular lens insertion device 1 (hereinafter, simply referred to as insertion device 1). FIG. 1A illustrates a plan view, and FIG. 1B illustrates a side view. The insertion device 1 has a nozzle main body 10 as a device main body, and a plunger 30 which is inserted into the nozzle main body 10 and can move back and forth. The nozzle main body 10 is formed in a cylindrical shape having a substantially rectangular cross-section, one side (hereinafter, a largely open side is referred to as a rear end portion 10b) thereof is largely opened, and a nozzle portion 15 as a thinly narrowed insertion tube, and an obliquely opened leading end portion 10a are included at the other side end thereof. Further, hereinafter, a direction from the leading end portion 10a of the nozzle main body 10 toward the rear end portion 10b or its opposite direction is referred to as a longitudinal direction, a direction perpendicular to the plane in FIG. 1A is referred to as a vertical direction, and a direction perpendicular to the plane in FIG. 1B is referred to as a horizontal direction.

In the vicinity of the rear end portion 10b of the nozzle main body 10, a hold portion 11 is integrally provided which protrudes in a plate shape and is caught by a user's finger when the user pushes the plunger 30 to the leading end side of the nozzle main body 10. Also, on the rear end side of the nozzle portion 15 in the nozzle main body 10, a stage portion 12 as a housing portion for setting the intraocular lens 2 is provided. The stage portion 12 is configured so that the upper side (a front side perpendicular to the plane in FIG. 1A which corresponds to an optical axis front side of the intraocular lens) of the nozzle main body 10 is opened by opening a stage lid portion 13. Further, a positioning member 50 is attached to the stage portion 12 from the lower side (a rear side perpendicular to the plane in FIG. 1A which corresponds to the optical axis rear side of the intraocular lens) of the nozzle main body 10. By the positioning member 50, the intraocular lens 2 is stably held in the stage portion 12 before use (during transport).

That is, in the insertion device 1, during manufacturing, in the state in which the stage lid portion 13 is opened and the positioning member 50 is attached to the stage portion 12, the intraocular lens 2 is set in the stage portion 12 so that the optical axis front side faces upward. Moreover, after closing the stage lid portion 13, the device is shipped and sold. Furthermore, a user detaches the positioning member 50 while closing the stage lid portion 13 in use, and then, pushes the plunger 30 to the leading end side of the nozzle main body 10. Thus, after pressing the intraocular lens 2 by the plunger 30 and moving it to the nozzle portion 15, the intraocular lens 2 is pushed from the leading end portion 10a. In addition, the nozzle main body 10, the plunger 30 and the positioning member 50 of the insertion device 1 are formed of a resin material such as polypropylene. Polypropylene is a material that has proven in medical devices and also has high reliability such as chemical resistance.

Figure 2A:
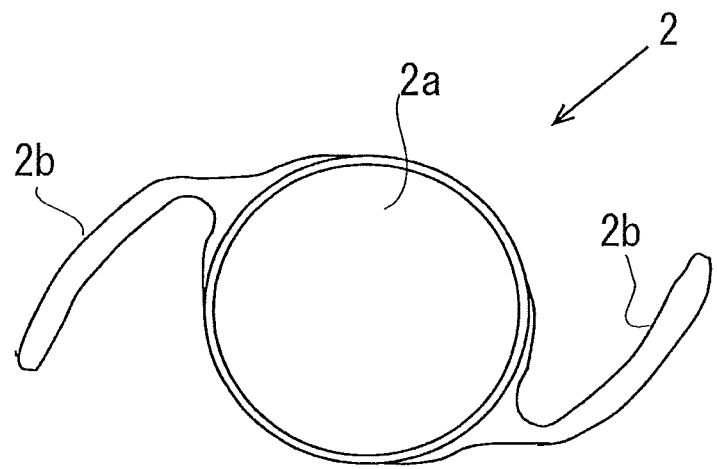
FIGS. 2A and 2B are diagrams illustrating a schematic configuration of the intraocular lens.
Figure 2B:
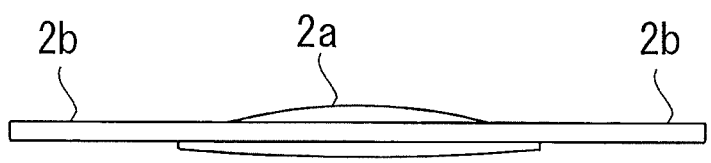

FIGS. 2A and 2B are diagrams illustrating a schematic configuration of the intraocular lens 2. FIG. 2A illustrates a plan view, and FIG. 2B illustrates a side view. The intraocular lens 2 is formed by a lens main body 2a having a predetermined refractive power, and two whisker-like support portions 2b and 2b which are provided integrally with the lens main body 2a to hold the lens main body 2a in the eyeball. The lens main body 2a and the support portion 2b are formed of a flexible resin material.

Figure 3:
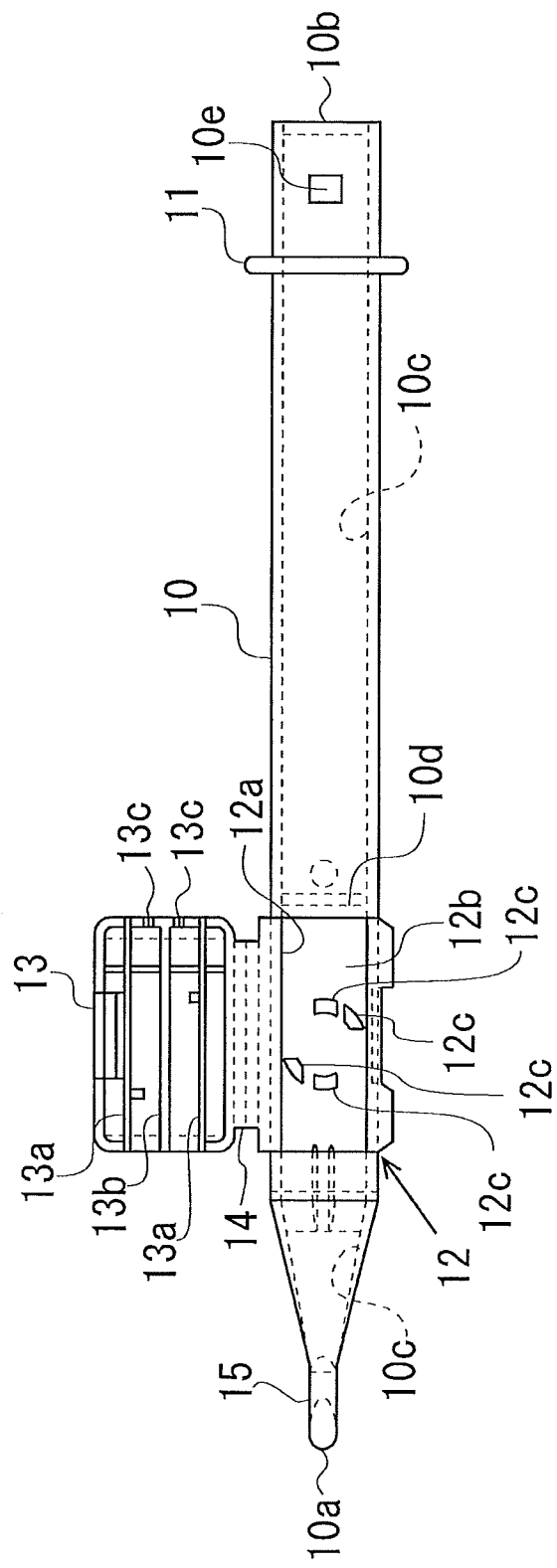
FIG. 3 is a diagram illustrating a schematic configuration of a conventional nozzle main body.

FIG. 3 illustrates a plan view of the nozzle main body 10. As described above, in the nozzle main body 10, intraocular lens 2 is set in the stage portion 12. The intraocular lens 2 is released from the leading end portion 10a by being pressed by the plunger 30 in that state. In addition, a through hole 10c is provided inside the nozzle main body 10. The cross-sectional shape of the through hole 10c varies in accordance with changes in the outer form of the nozzle main body 10. Moreover, when the intraocular lens 2 is released, the intraocular lens 2 is deformed in accordance with the changes in cross-sectional shape of the through hole 10c in the nozzle main body 10, and is released after being deformed to a shape that easily enters the incision formed in the patient's eyeball. Further, the leading end portion 10a has an obliquely cut shape so that the upper side is located on the front side of the lower side (as it goes from the optical axis rear side of the housed intraocular lens 2 to the front side, the position of the end surface is located on the more front side in the insertion direction of the intraocular lens). In addition, the obliquely cut shape of the leading end portion 10a may be a plane when viewed from the horizontal direction, that is, a linearly obliquely cut shape, and may be obliquely cut so as to have a bulge on the outside, that is, a curved surface shape.

The stage portion 12 is formed with a stage groove 12a having a width that is slightly greater than the diameter of the lens main body 2a of the intraocular lens 2. A longitudinal dimension of the stage groove 12a is set to be greater than a maximum width dimension including the support portions 2b and 2b that extend on both sides of the intraocular lens 2. Also, a set surface 12b is formed by a bottom surface of the stage groove 12a. A vertical position of the set surface 12b (a position in a direction perpendicular to the plane of FIG. 3) is set on the upper part (front side in the direction perpendicular to the plane of FIG. 3) of the height position of the bottom surface of the through hole 10c of the nozzle main body 10, and the set surface 12b and the bottom surface of the through hole 10c are connected by a bottom inclined surface 10d.

The stage portion 12 and the stage lid portion 13 are integrally formed. The stage lid portion 13 has a longitudinal dimension equivalent to the stage portion 12. The stage lid portion 13 is connected by a thin-plate-shaped connecting portion 14 formed by extension of the side surface of the stage portion 12 to the stage lid portion 13. The connecting portion 14 is flexibly formed at a central portion, and the stage lid portion 13 is adapted to be able to be overlap-closed on the stage portion 12 from the upper side by bending the connecting portion 14.

In the stage lid portion 13, on a surface facing the set surface 12b when closing, ribs 13a and 13b are provided so as to reinforce the stage lid portion 13 and stabilize the position of the intraocular lens 2. In addition, a guide projection 13c is provided as a guide on the upper side of the plunger 30.

Figure 4A:
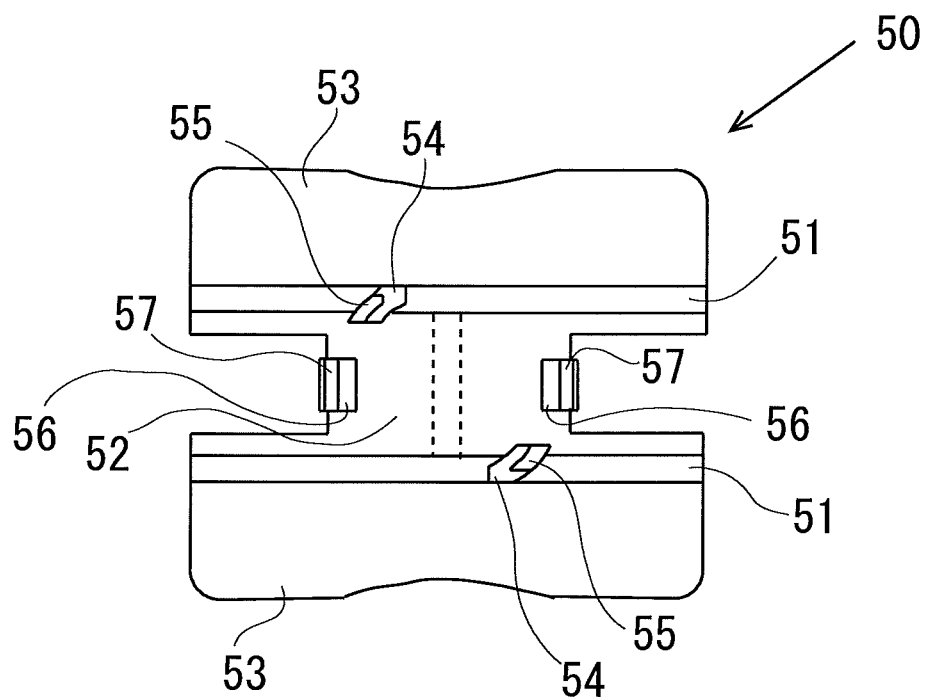
FIGS. 4A and 4B are diagrams illustrating a schematic configuration of a conventional positioning member.
Figure 4B:
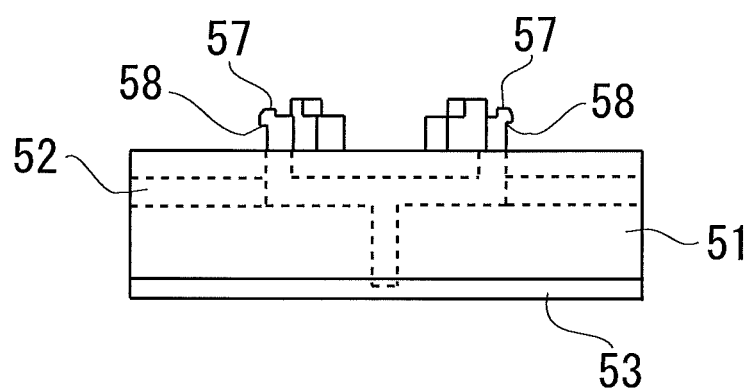

A positioning member 50 is detachably provided on the lower side of the set surface 12b of the stage portion 12. FIGS. 4A and 4B illustrate a schematic configuration of the positioning member 50. FIG. 4A illustrates a plan view, and FIG. 4B illustrates a side view. The positioning member 50 is configured as a separate body from the nozzle main body 10, and has a structure in which a pair of side wall portions 51 and 51 is connected by a connecting portion 52. At lower ends of each side wall portions 51, holding portions 53 and 53 are formed which extend and spread outward.

Moreover, at the upper end portions of each side wall portion 51 and 51, a pair of first placing portions 54 and 54 is formed which has a circular arc shape as viewed from the upper part and protrudes upward. Furthermore, on an outer circumferential side on the upper end surface of the first placing portion 54, first positioning portions 55 and 55 are formed to protrude. A distance between the inner diameters of the first positioning portions 55 is set to be slightly greater than the diameter of the lens main body 2a of the intraocular lens 2.

In addition, at the both longitudinal ends of the connecting portion 52, a pair of second placing portions 56 and 56 is formed which has a rectangular shape as viewed from the upper part and protrudes upward. The height of the upper surfaces of the second placing portions 56 is equal to the height of the upper surfaces of the first placing portions 54. In addition, at the outer portions on the upper surfaces of the second placing portions 56 and 56, second positioning portions 57 and 57 are formed which further protrude upward over the whole horizontal direction of the second placing portions 56. A distance between the inner sides of the second positioning portions 57 is set to be slightly greater than the diameter of the lens main body 2a of the intraocular lens 2. In addition, at the upper end portions of the second placing portions 56, locking claws 58 and 58 are formed which slightly protrude in the longitudinal direction over the whole horizontal direction.

In this example, the positioning members 50 are assembled from the lower side of the set surface 12b of the nozzle main body 10. On the set surface 12b of the nozzle main body 10, a set surface through hole 12c penetrating through the set surface 12b in the thickness direction is formed. The outer form of the set surface through hole 12c has a slightly larger and substantially similar shape to the shape obtained when the first placing portion 54 and the second placing portion 56 of the positioning member 50 are viewed from the upper side. Moreover, when the positioning member 50 is attached to the nozzle main body 10, the first placing portions 54 and 54 and the second placing portions 56 and 56 are inserted into the set surface through hole 12c from the lower side of the set surface 12b, and protrude to the upper side of the set surface 12b.

At that time, the locking claws 58 and 58 provided on the second positioning portions 57, 57 protrude to the set surface 12b via the set surface through hole 12c, and are locked on the upper surface of the set surface 12b. Thus, the positioning member 50 is assembled from the lower side of the nozzle main body 10, and the first placing portions 54 and 54 and the second placing portions 56 and 56 are fixed in the state of protruding from the set surface 12b. Moreover, when the intraocular lens 2 is set in the set surface 12b, the outer circumferential portion bottom surface of the lens main body 2a is placed on the upper surfaces of the first placing portions 54 and 54 and the second placing portions 56 and 56. Also, the lens main body 2a is subjected to the position regulation with respect to the horizontal direction by the first positioning portions 55, 55 and the second positioning portions 57 and 57.

FIGS. 5A and 5B illustrate a schematic configuration of a conventional plunger 30. The plunger 30 has a length in the front and rear direction that is slightly greater than the nozzle main body 10. Moreover, the plunger 30 is formed by an acting portion 31 of a leading end side based on a cylindrical shape, and an insertion portion 32 of a rear end side based on a rectangular rod shape. The acting portion 31 is configured to include a cylindrical portion 31a having a cylindrical shape, and a thin plate-shaped flat portion 31b extending in the horizontal direction of the cylindrical portion 31a.

In the leading end portion of the acting portion 31, a notch portion 31c is formed. As can be seen from FIGS. 5A and 5B, the notch portion 31c is formed in a groove shape which is opened in the upward direction of the acting portion 31 and penetrates in the horizontal direction. Also, as can be seen from FIG. 5B, the groove wall of the leading end side of the notch portion 31c is formed by an inclined surface which is directed upward as it goes to the leading end side of the acting portion 31.

Meanwhile, the insertion portion 32 generally has a substantially H-shaped cross-section, and its horizontal and vertical dimensions are set to be slightly smaller than those of the through hole 10c of the nozzle main body 10. Also, at the rear end of the insertion portion 32, a disk-shaped pressing plate portion 33 extending in the vertical and horizontal directions is formed.

In a portion of the leading end side from the center in the longitudinal direction of the insertion portion 32, a claw portion 32a is formed which protrudes toward the upper side of the insertion portion and is vertically movable by elasticity of the material of the plunger 30. Moreover, when the plunger 30 is inserted into the nozzle main body 10, the locking hole 10e and the claw portion 32a as illustrated in FIG. 3 provided in the thickness direction on the upper surface of the nozzle main body 10 are engaged with each other, and thus, a relative position between the nozzle main body 10 and the plunger 30 in the initial state is determined. The formation positions of the claw portion 32a and the locking hole 10e are set so that, in the engaged state, the leading end of the acting portion 31 is located behind the lens main body 2a of the intraocular lens 2 set in the stage portion 12 and is located at a position where the notch portion 31c can support the support portion 2b behind the lens main body 2a from the lower part.

Before housing the intraocular lens 2 in the insertion device 1 configured as described above, the plunger 30 is inserted into the nozzle main body 10 and arranged at an initial position. Further, as described above, the positioning member 50 is attached to the nozzle main body 10 from the lower part of the set surface 12b. Thus, the first placing portion 54 and the second placing portion 56 of the positioning member 50 are held in a state of protruding to the set surface 12b.

Next, the lens main body 2a of the intraocular lens 2 is placed and positioned on the upper surfaces of the first placing portion 54 and the second placing portion 56 in the state of directing the support portions 2b and 2b in the longitudinal direction of the nozzle main body 10. In this state, since the outer peripheral portion of the lens main body 2a is in contact with the first placing portion 54 and the second placing portion 56, the central portion of the intraocular lens 2 is supported in a non-load state. Further, in this state, the rear support portion 2b of the intraocular lens 2 is supported by the bottom surface of the notch portion 31c of the plunger 30.

When the intraocular lens 2 is inserted into the eyeball using the insertion device 1, first, the positioning member 50 is detached from the nozzle main body 10. Thus, the first placing portion 54 and the second placing portion 56 supporting the lens main body 2a of the intraocular lens 2 are retracted from the set surface 12b, and the intraocular lens 2 is movably placed on the set surface 12b.

Next, the leading end portion 10a of the nozzle portion 15 of the nozzle main body 10 is inserted into the incision provided in the eye tissue. Here, since the leading end portion 10a has an oblique opening shape, it is possible to easily perform the insertion into the incision. Moreover, after inserting the nozzle portion 15 to the incision, the pressing plate portion 33 of the plunger 30 is pushed to the leading end side of the nozzle main body 10 in that state. Thus, the leading end of the acting portion 31 of the plunger 30 abuts against the outer circumference of the lens main body 2a of the intraocular lens 2 that is set in the set surface 12a, and the intraocular lens 2 is guided toward the leading end portion 10a by the plunger 30. In addition, as described above, the opening shape of the leading end portion 10a may be an oblique opening shape in which the opening surface is flat, that is, linear, and may be an oblique opening shape which has a bulge on the outside, that is, a curved surface shape.

In a surgery which inserts the intraocular lens 2 into an eyeball of a patient using the insertion device 1 of the conventional intraocular lens as described above, when pressing the intraocular lens 2 by the plunger 30, the leading end of the acting portion 31 does not necessarily press the center of gravity of the lens main body 2a of the intraocular lens 2. Also, at the moment when the intraocular lens is released from the leading end portion 10a, there is a state in which only the upper side is held by the leading end portion 10a end portion and the lower side is not held. Thus, there has been a tendency for the intraocular lens 2 to rotate so as to perform the forward rolling when the intraocular lens 2 is released from the leading end portion 10a of the nozzle portion 15. Further, there has been a case where the lens main body 2a of the intraocular lens 2 is interposed between the through hole 10c (the inner wall of the nozzle main body 10) near the leading end portion 10a and the acting portion 31 of the plunger 30, and the intraocular lens 2 is not smoothly released from the leading end portion 10a.

Figure 6C:
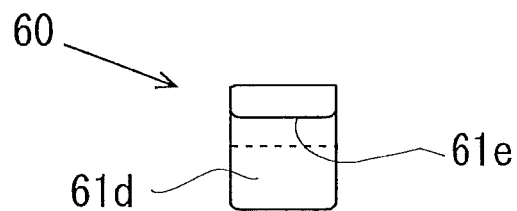
FIGS. 6A to 6C are diagrams illustrating the vicinity of a leading end of the plunger in a first example of the present invention.
Figure 6A:
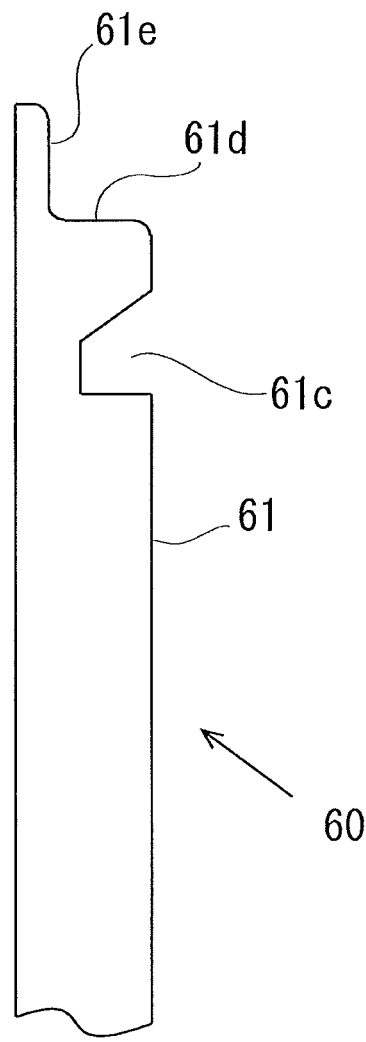
Figure 6B:
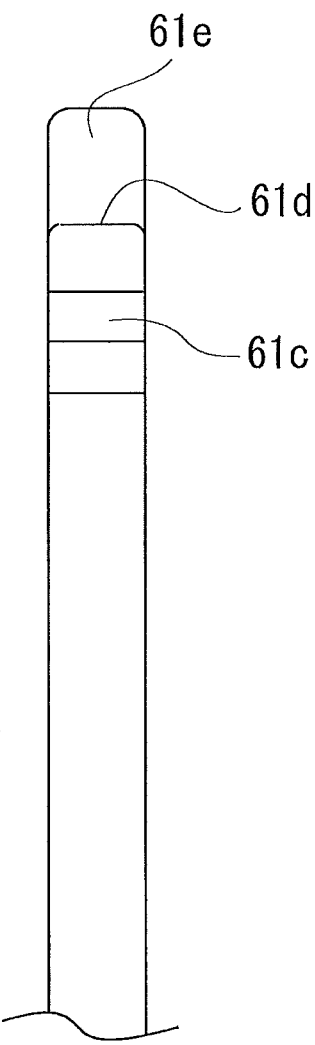

In contrast, in this example, by changing the leading end shape of the acting portion of the plunger, the intraocular lens 2 is more smoothly released from the leading end portion 10a of the nozzle portion 15, while maintaining the posture. FIGS. 6A to 6C illustrate a shape near the leading end of an acting portion 61 of a plunger 60 in this example. FIG. 6A illustrates a side view, FIG. 6B illustrates a plan view, and FIG. 6C illustrates a front view. As illustrated in FIGS. 6A to 6C, in this example, a protrusion 61e as a protruding portion in which the lens main body 2a is placed is provided on the lower side (the optical axis rear side of the intraocular lens 2) of a leading end 61d of the acting portion 61.

FIGS. 7A and 7B are diagrams for describing a positional relation before and after the operation between the plunger 60 and the intraocular lens 2 in this example. FIG. 7A illustrates a plan view in a state before starting an inserting operation of the intraocular lens 2, and FIG. 7B illustrates a side view of the same state. As illustrated in FIGS. 7A and 7B, in this example, the rear support portion 2b of the intraocular lens 2 is also supported by a notch portion 61c of the acting portion 61 of the plunger 60 from the lower side.

Moreover, in the state before starting the operation of inserting the intraocular lens 2, that is, in a state in which the positioning member 50 is attached to the stage portion 12, and the locking hole 10e illustrated in FIG. 3 provided in the nozzle main body 10 is engaged with a pawl portion (not illustrated) of the plunger 60, the upper surface of the protrusion 61e is located below the lens main body 2a of the intraocular lens 2, and the leading end of the protrusion 61e becomes a state of slightly entering toward the center from the outer circumference of the lens main body 2a.

Moreover, as illustrated by an arrow in FIG. 7B, by removing the positioning member 50 from the stage portion 12, the position of the intraocular lens 2 is relatively lowered. Moreover, the outer circumferential portion of the lens main body 2a of the intraocular lens 2 is placed on the protrusion 61e.

Next, when the plunger 60 is pushed into the nozzle main body 10, in the state in which the outer circumferential portion of the lens main body 2a of the intraocular lens 2 is placed on the upper surface of the protrusion 61e, the plunger 60 moves forward (left side of FIGS. 7A and 7B), and the leading end 61d abuts against the outer circumferential portion of the lens main body 2a from the horizontal direction. Moreover, when the plunger 60 is pushed into the nozzle main body 10, the leading end 61d presses the outer circumferential portion of the lens main body 2a to move the intraocular lens 2 to the nozzle portion 15 and release the intraocular lens 2 from the leading end portion 10a.

Figure 8A:
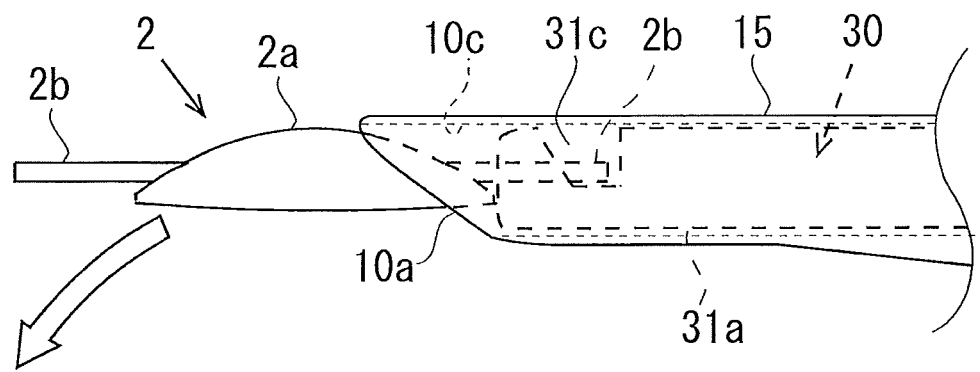
FIGS. 8A and 8B are diagrams illustrating the operation of the insertion device in the first example of the present invention.
Figure 8B:
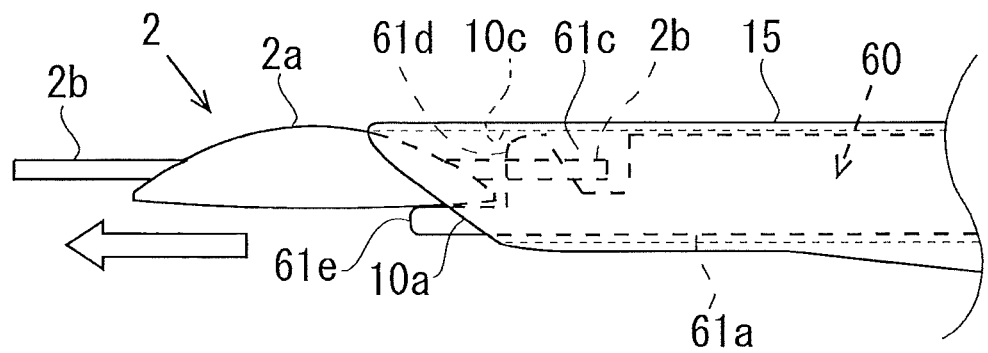

FIGS. 8A and 8B are diagrams for describing a state when the intraocular lens 2 is released from the leading end portion 10a of the nozzle portion 15. FIG. 8A illustrates a case of being pushed by conventional plunger 30, and FIG. 8B illustrates a case of being pushed by the plunger 60 of this example. In addition, the intraocular lens 2 in FIGS. 8A and 8B is deformed with the change in cross-sectional shape of the through hole 10c, and the vertical width dimension increases.

In the conventional case illustrated in FIG. 8A, when the intraocular lens 2 is released from the leading end portion 10a, since the intraocular lens 2 is not held on the lower side (the optical axis rear side of the lens main body 2a), moment due to own weight acts on the intraocular lens 2, and the intraocular lens 2 has tended to perform forward rolling in the direction of the arrow in FIG. 8A. Thus, when releasing the intraocular lens 2 into the eyeball, in some cases, it has been difficult to maintain the posture of the lens main body 2a, and there has been a need to significantly adjust the posture of the intraocular lens 2 after release.

In contrast, in this example illustrated in FIG. 8B, the lens main body 2a is held so as to be interposed by the upper surface of the protrusion 61e and the upper inner wall of the through hole 10c from the top and bottom. Therefore, in this example, as illustrated in FIG. 8B, the intraocular lens 2 may be released while maintaining the posture, in the pressing direction by the plunger 60.

Further, in the conventional example illustrated in FIG. 8A, there has been a case where the lens main body 2a of the intraocular lens 2 is interposed in a gap between the outer wall of the acting portion 31 of the plunger 30 and the through hole 10c and is not smoothly released. In contrast, in this example illustrated in FIG. 8B, since the lens main body 2a of the intraocular lens 2 is stably supported by the protrusion 61e and the leading end 61d, it is possible to suppress the inconvenience such as being interposed in the gap between the outer wall of the acting portion 31 of the plunger 30 and the through hole 10c.

In addition, in this example, the upper region of the leading end portion 10a of the nozzle main body 15 corresponds to a "partial region" which is the front side of the insertion direction of the intraocular lens in the leading end of the insertion tube. In this example, on the lower side (the optical axis rear side of the intraocular lens 2) of the leading end 61d of the acting portion 61, the protrusion 61e is provided on which the lens main body 2a is placed. This means that at the leading end of the plunger, in a portion opposite to the "partial region" of the leading end of the insertion tube as viewed from the front side in the insertion direction of the intraocular lens at the timing of inserting the intraocular lens, the protruding portion protruding to the front side of the insertion direction of the intraocular lens so as to be able to place a part of the intraocular lens is provided.

Meanwhile, as illustrated in FIGS. 8A and 8B, in the through hole 10c of this example, the cross-sectional shape changes so that the width dimension of the bottom and top surfaces decrease as it goes from the stage portion 12 side to the nozzle portion 15 side. By this change, when the intraocular lens 2 is released from the leading end portion 10c, the intraocular lens 2 is deformed in a manner surrounding the axis of movement direction so as to be convex upward or be convex downward. Thus, it is possible to insert the intraocular lens 2 into the eyeball even from a small incision.

In this case, when considering the use of the plunger 60 of this example, in the case where the intraocular lens 2 is deformed so as to be convexed downward, it is possible to more reliably hold the convexed portion on the upper surface of the protrusion 61e. Further, even when the lens main body 2a of the intraocular lens 2 is restored to an original shape just after release, in the case of being deformed so as to be convexed downward, it is easy to maintain the holding state by the protrusion 61e. Therefore, in this example, in accordance with the use of the plunger 60, a mechanism which promotes the deformation such that the intraocular lens 2 is convexed downward is provided in the nozzle main body 10.

Figure 9A:
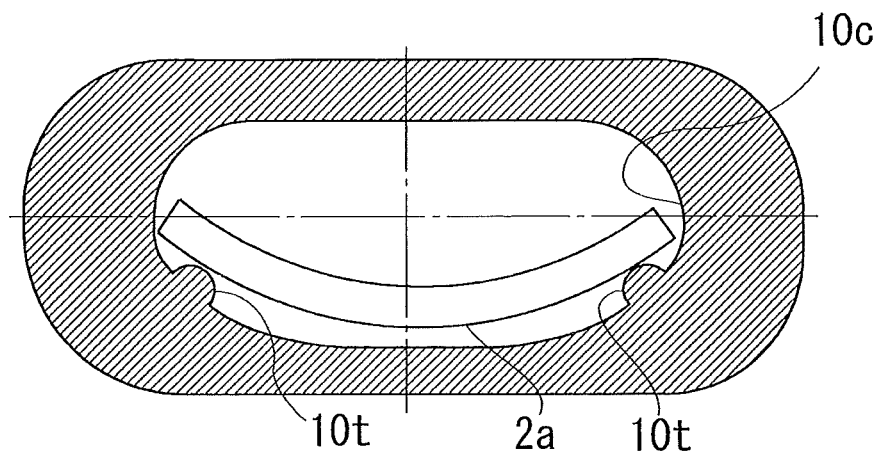
FIGS. 9A to 9C are diagrams illustrating a deformed state of the lens main body of the intraocular lens in the first example of the present invention.
Figure 9B:
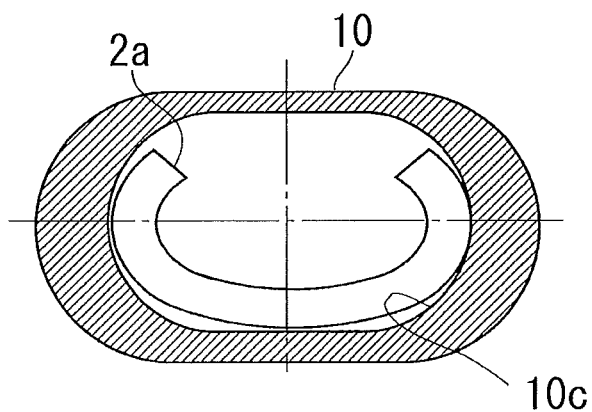
Figure 9C:
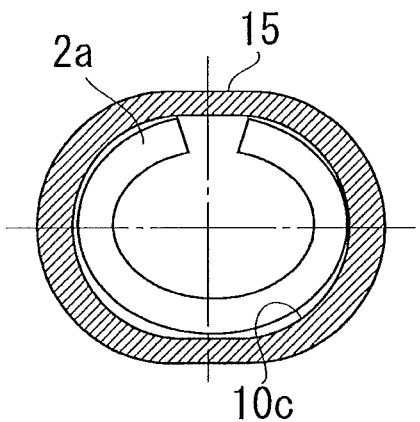

FIGS. 9A to 9C illustrate cross-sectional views of the nozzle main body 10 of this example. FIG. 9A is a cross-sectional view just after starting the movement by pressing the intraocular lens 2 by the plunger 60, FIG. 9B is a cross-sectional view thereafter in the middle of decreasing in the width dimensions of the bottom surface and the top surface as it goes from the stage portion 12 side to the nozzle portion 15 side as illustrated in FIG. 3, and FIG. 9C illustrates a cross-sectional view when the intraocular lens 2 passes through the nozzle portion 15. Also, each cross-sectional view illustrates the shape of the lens main body 2a of the intraocular lens 2 when passing through the cross-section. As can be seen from FIG. 9A, in the through hole 10c before the cross-section changes just in front of the stage portion 12 in this example, guides 10t and 10t are formed which come into contact with the left and right outer circumferential portions of the lens main body 2a from the lower side.

Before at least the intraocular lens 2 passes through a region in which the cross-section of the through hole 10c becomes smaller in a tapered shape, the guides 10t and 10t guide the lens main body 2a so that the left and right outer circumferential portions of the lens main body 2a are not displaced downward, and thus, it is possible to promote that the intraocular lens 2 is convexed downward in FIGS. 9A to 9C. That is, as illustrated in FIG. 9B and FIG. 9C, it is possible to more reliably deform the lens main body 2a so as to be convexed downward in FIGS. 9A to 9C.

Thus, it is possible to more reliably place the convexed portion of the lens main body 2a on the upper surface of the protrusion 61e, and it is possible to more stably hold the intraocular lens 2 by the protrusion 61e. Further, the guides 10t, 10t correspond to the lens deforming unit in this example. In this example, as the lens deforming unit, although the guides 10t, 10t provided in the through hole 10c of the nozzle main body 10 has been illustrated, the lens deforming unit may have other configurations. For example, the cross-section of the nozzle main body 10 may have a configuration which is reduced by two-stage tapers of a first gradual taper portion and a second taper portion having a taper sharper than the first taper portion. Also, it may be a guide provided in a convexed shape to the lower side (lens optical axis rear side) at the center of the upper side (lens optical axis front side) of through hole 10c.

Also, although this example describes the plunger 60 in which the acting portion 61 has a prismatic shape in the cross-section as illustrated in FIGS. 6A to 6C as an example, this is merely an example, and it is a matter of course that the shape of the plunger including the acting portion 61 may be other shapes, without departing from the gist of the present invention. This also applies to the shapes of the nozzle main body, the nozzle portion or the like.

Second Example

Next, a second example of the present invention will be described. The second example illustrates an example in which a notch portion for supporting the rear support portion of the intraocular lens in the plunger is provided on the lower side (the optical axis rear side of the intraocular lens) of the plunger.

FIGS. 10A to 10E are diagrams in the vicinity of the leading end of an acting portion 71 of a plunger 70 of this example. This example differs from the plunger 60 of the first example in that, in the plunger 60 of the first example, the notch portion 61c for supporting the support portion 2b is disposed on the upper side (optical axis front side of the intraocular lens 2), like the conventional example, and meanwhile, the notch portion 71c of this example is disposed on the lower side (the optical axis rear side of the intraocular lens 2).

In FIGS. 10A to 10E, FIGS. 10A and 10C are side views when viewed from the horizontal direction, respectively, FIG. 10B is a plan view when viewed from the optical axis front side of the intraocular lens 2, FIG. 10D is a bottom view when viewed from the optical axis rear side of the intraocular lens 2, and FIG. 10E is a front view. As can be seen from FIGS. 10A to 10E, in the plunger 70 of this example, a protrusion 71e is provided at a leading end 71d of the acting portion 71, and the notch portion 71c for holding the support portion 2b of the intraocular lens 2 is provided on the optical axis rear side of the intraocular lens 2 of the acting portion 71.

FIGS. 11A and 11B are diagrams for describing the positional relation between the plunger 70 and the intraocular lens 2 in this example. FIG. 11A is a side view in a state before starting the operation of inserting the intraocular lens 2, and FIG. 11B illustrates a bottom view when the same state is viewed from the bottom. As illustrated in FIGS. 11A and 11B, even in this example, in the state before starting the operation of inserting the intraocular lens 2, that is, in the state in which the positioning member 50 is attached to the stage portion 12, the locking hole 10e illustrated in FIG. 3 provided in the nozzle main body 10 is engaged with a pawl portion (not illustrated) of the plunger 70, the upper surface of the protrusion 71e is located below the lens main body 2a of the intraocular lens 2, and the leading end of the protrusion 71e is in the state of slightly entering toward the center from the outer circumference side of the lens main body 2a. Further, in this example, the rear support portion 2b of the intraocular lens 2 is held in the form of penetrating the notch portion 71c provided on the lower side of the acting portion 71 of the plunger 70.

Moreover, by removing the positioning member 50 from the stage portion 12, as illustrated by an arrow in FIG. 11A, the position of the intraocular lens 2 is relatively lowered. The outer circumferential portion of the lens main body 2a of the intraocular lens 2 is placed on the protrusion 71e. At that time, the rear support portion 2b of the intraocular lens 2 moves in the notch portion 71c so that its position is lowered similarly to the lens main body 2a.

Furthermore, when the plunger 70 is pushed into the nozzle main body 10, in the state in which the lens main body 2a of the intraocular lens 2 is placed on the upper surface of the protrusion 71e, the plunger 70 moves forward (left side of FIGS. 11A and 11B), and the leading end 71d abuts against the outer circumferential portion of the lens main body 2a. Moreover, when the plunger 70 is pushed into the nozzle main body 10, the leading end 71d presses the outer circumferential portion of the lens main body 2a to move the intraocular lens 2 to the nozzle portion 15. At that time, the rear support portion 2b of the intraocular lens 2 moves in the notch portion 71c, while being held so that inadvertent deformation does not occur.

In this example, when the plunger 70 is further pushed, the intraocular lens 2 reaches the leading end portion 10a of the nozzle portion 15. Moreover, as in the first example, when the intraocular lens 2 is released from the leading end portion 10a, the lens main body 2a of the intraocular lens 2 is straightly released forward, in the state in which the upper side is supported on the wall surface of the through hole 10c and the lower side is supported on the protrusion 71e.

Moreover, thereafter, the acting portion 71 of the plunger 70 protrudes from the leading end portion 10a, and the notch portion 71c is also exposed to the outside from the leading end portion 10a. Then, the support portion 2b of the intraocular lens 2 held in the notch portion 71c is smoothly detached from the plunger 70 by its own weight. Thus, inconvenience such as a situation in which the support portion 2b is caught on the plunger 70 does not occur, and it is possible to more smoothly release the intraocular lens 2 into the eyeball.

When adopting the configuration of the plunger 70 as in this example, when setting the intraocular lens 2 in the stage portion 12, it is desirable to set the intraocular lens 2 from the lower side. The reason is that, there is a difficulty in setting the intraocular lens 2 in the stage portion 12 from the upper side (optical axis front side) so that the notch portion 71c holds the support portion 2b in the state in which the support portion 2b of the intraocular lens 2 penetrates through the notch portion 71c which is opened downward, and this setting hinders the simplification of the work.

In order to overcome the above-described inconvenience, in the insertion device of this example, a configuration is provided in which the stage lid portion may be provided on the lower side (optical axis rear side of the intraocular lens 2) of the nozzle main body, and the positioning member can be attached from the upper side (the optical axis front side of the intraocular lens 2), and when the intraocular lens 2 is set in the stage portion, the intraocular lens 2 may be set from the lower side (the optical axis rear side).

Figure 12:
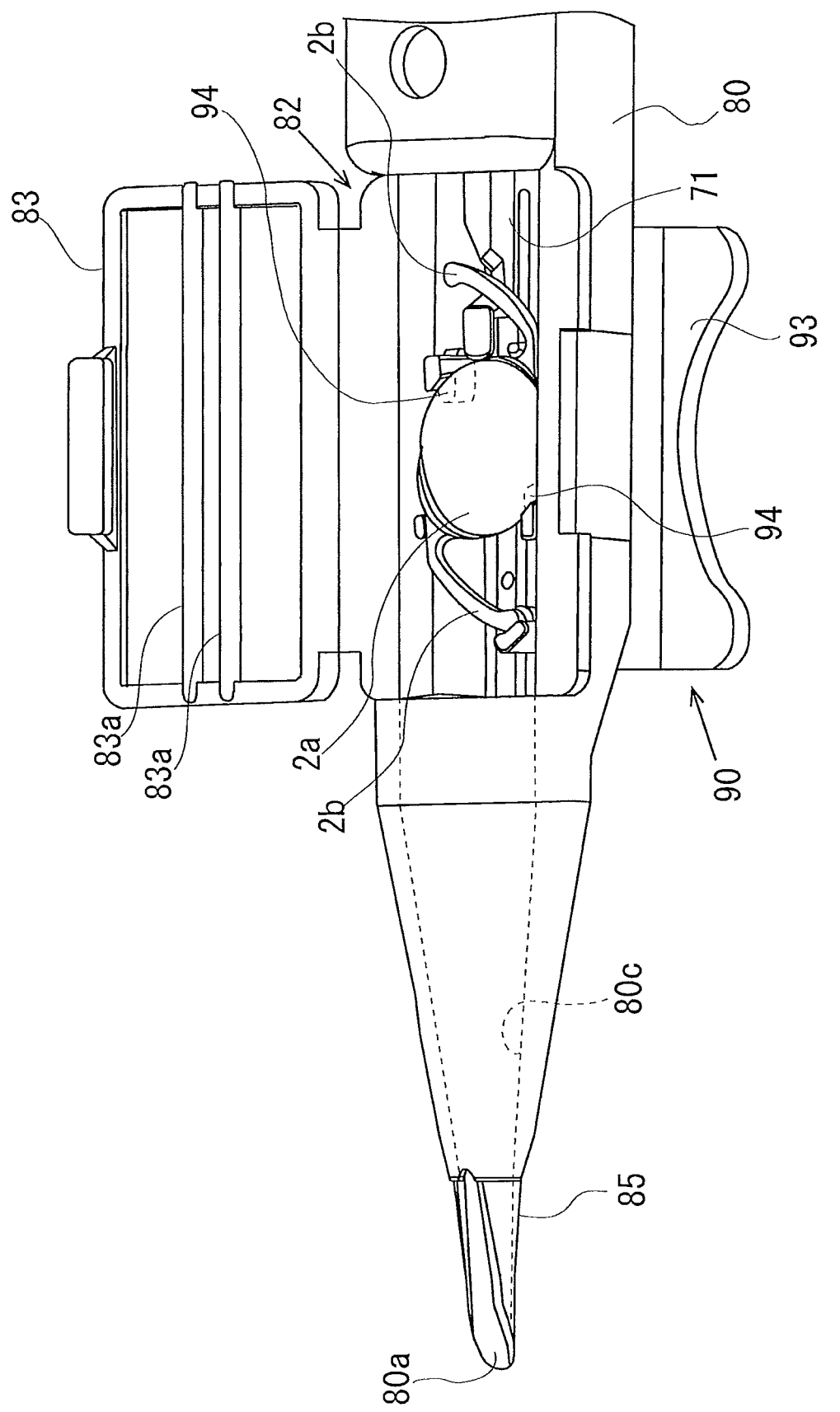
FIG. 12 is a perspective view illustrating the vicinity of a housing portion of the insertion device in the second example of the present invention.

FIG. 12 is a perspective view when viewed from an oblique direction of the lower side (lens optical axis rear side) which illustrates the vicinity of a stage portion 82 in a nozzle main body 80 of an insertion device in such a case. As can be seen from FIG. 12, in this configuration example, a stage lid portion 83 is provided on the lower side (the optical axis rear side of the intraocular lens) in the nozzle main body 80. Therefore, when the intraocular lens 2 is set in the stage portion 82, after the stage lid portion 83 comes upward (opposite direction to the ground) by turning the nozzle main body 80 upside down, the intraocular lens 2 is set. In this state, the holding portion 93 of the positioning member 90 protrudes downward (ground direction).

In this state, the intraocular lens 2 is set in the stage portion 83 of the nozzle main body 80. At this time, since the notch portion 71c of the plunger 70 is in a state in which the upward direction (the direction opposite to the ground) is opened, it is possible to easily hold the rear support portion 2a of the intraocular lens 2 in the notch portion 71c. Thereafter, by closing the stage lid portion 83, detaching the positioning member 90 and returning the top and the bottom of the nozzle main body to the original state, setting of the intraocular lens 2 to the stage portion 82 is completed.

Here, differences of the detailed configuration and operation of the stage lid portion 83 and the positioning member 90 from those of the stage lid portion 13 and the positioning member 50 in the first example are as follows. First, the first placing portion 94 configured to regulate the height direction position of the lens main body 2a in the positioning member 90 comes into contact with the optical surface of the optical axis front side of the lens main body 2a of the intraocular lens 2 in this example, but it has a structure which comes into contact with only the outside of the actual use region. Further, the difference from the first example is that a guidance guide 83a of the plunger 70 is provided on the inner wall surface of the stage lid portion 83.

As described, according to this example, it is possible to suppress inconveniences such as a situation, in which, when the intraocular lens 2 is released from the leading end portions 10a and 80a of the nozzle portions 15 and 85, the intraocular lens 2 rotates in the forward rolling direction, or is interposed between the through holes 10c and 80c near the leading end portions 10a and 80a and the outer wall of the acting portion 71 of the plunger 70, and it is possible to more smoothly release the intraocular lens 2 into the eyeball. Further, in this example, since the notch portion 71c of the plunger 70 is provided on the lower side (the optical axis rear side of the intraocular lens 2), when inserting the intraocular lens 2 into the eyeball, the rear support portion 2a can be more reliably detached from the plunger 70, and the intraocular lens 2 can be more reliably released into the eyeball. Also, since it is possible to suppress the operation of the elastic deformation and restoration of the support portion 2b, it is possible to suppress the influence to the position adjustment such as the posture change of the intraocular lens 2.

In addition, in the above-mentioned examples, although the one-piece type intraocular lens in which the lens main body 2a and the support portions 2b and 2b of the intraocular lens 2 are integrally molded has been described as an example, it is needless to say that the present invention is also applicable to a three-piece type intraocular lens in which the support portions 2b and 2b and the lens main body 2a are formed by another members.

In addition, in the above-mentioned examples, an example in which the leading end portion 10a has an obliquely cut shape so that the upper side is located on the front side of the lower side (as it goes from the optical axis rear side of the housed intraocular lens 2 toward the front side, the position of the end surface is located on the more front side in the insertion direction of the intraocular lens). However, the present invention is not limited to this configuration.

For example, the leading end portion of the nozzle portion may have an obliquely cut shape so that the lower side is located on the front side of the upper side (as it goes from the optical axis front side of the housed intraocular lens 2 toward the rear side, the position of the end surface is located on the more front side in the insertion direction of the intraocular lens). In this case, on the upper side (the optical axis front side of the intraocular lens 2) of the leading end of the acting portion of the plunger, a protrusion as a protruding portion on which the lens main body 2a is placed may be provided.

In this case, the lens main body 2a is held so as to be interposed by the lower surface of the protrusion and the lower inner wall of the through hole 10c from the top and bottom. This also makes it possible to release intraocular lens 2, while maintaining the posture in the pressing direction by the plunger.

REFERENCE SIGNS LIST 1 insertion device
2 intraocular lens
10, 80 nozzle main body
10a, 80a leading end portion
10b rear end portion
12, 82 stage portion
13, 83 stage lid portion
15, 85 insertion tube 30, 60, 70 plunger
31, 61, 71 acting portion
31a cylindrical portion
31b flat portion
50, 90 positioning member
61c, 71c notch portion
61d, 71d leading end
61e, 71e protrusion

What is claimed is:

1. An intraocular lens insertion device comprising:
a device main body that has an insertion tube to be inserted into an incision formed in an ocular tissue and is formed in a substantially cylindrical shape;
a housing portion that is provided integrally or separately in the device main body and is able to dispose the intraocular lens in the device main body by housing the intraocular lens; and
a plunger that is pushed to the device main body and presses the intraocular lens housed in the housing portion by a leading end, thereby releasing the intraocular lens from the leading end of the insertion tube into an eyeball,
the intraocular lens being inserted into the eyeball by releasing the intraocular lens from the leading end of the insertion tube inserted into the eyeball from the incision into the eyeball,
wherein the leading end of the insertion tube is obliquely cut so that its partial region is located on a front side in an insertion direction of the intraocular lens, and
at the leading end of the plunger, in a portion on an opposite side to the region of the leading end of the insertion tube when viewed from the front side in the insertion direction of the intraocular lens when inserting the intraocular lens, a protruding portion is provided which protrudes to the front side in the insertion direction of the intraocular lens, from the underside of the leading end of the plunger, so as to be able to place a part of the intraocular lens, and the portion other than the protruding portion of the leading end of the plunger is a face which is able to abut against the outer circumferential portion of the intraocular lens from the horizontal direction and is able to press and release the intraocular lens.

2. The intraocular lens insertion device according to claim 1, wherein the leading end of the insertion tube is obliquely cut so that, as the leading end goes toward the front side from an optical axis rear side of the intraocular lens housed in the housing portion, a position of an end surface is located on the more front side in the insertion direction of the intraocular lens, and
the protruding portion is provided so as to be able to place a surface of the optical axis rear side of the intraocular lens when inserting the intraocular lens.

3. The intraocular lens insertion device according to claim 2, further comprising:
a lens deforming unit for deforming the intraocular lens so as to be convexed to the optical axis rear side, when the intraocular lens is released into the eyeball from the leading end of the insertion tube by pressing the intraocular lens housed in the housing portion by the plunger.

4. The intraocular lens insertion device according to claim 3, wherein the intraocular lens insertion device is a preset type insertion device in which the intraocular lens is housed in the housing portion in advance in a manufacturing process, and which is distributed in a state in which the intraocular lens is housed.

5. The intraocular lens insertion device according to claim 2, wherein the intraocular lens insertion device is a preset type insertion device in which the intraocular lens is housed in the housing portion in advance in a manufacturing process, and which is distributed in a state in which the intraocular lens is housed.

6. The intraocular lens insertion device according to claim 1, wherein the intraocular lens insertion device is a preset type insertion device in which the intraocular lens is housed in the housing portion in advance in a manufacturing process, and which is distributed in a state in which the intraocular lens is housed.

* * * * *